United States Patent [19]

Berger

[11] 4,033,934

[45] July 5, 1977

[54] ALKENYL THIOALKYL SILICONES AND METHOD OF PREPARATION

[75] Inventor: Abe Berger, Schenectady, N.Y.

[73] Assignees: Abe Berger; Gerhard K. Adam, both of Schenectady, N.Y.; John Stonkus, Dover, N.J.

[22] Filed: Feb. 27, 1976

[21] Appl. No.: 662,149

[52] U.S. Cl. .................. 260/46.5 G; 260/46.5 E; 260/448.2 N; 260/448.8 R
[51] Int. Cl.$^2$ ..................................... C08G 77/04
[58] Field of Search ............. 260/46.5 E, 46.5 G, 260/448.8 R, 448.2 N

[56] References Cited

UNITED STATES PATENTS

| | | | |
|---|---|---|---|
| 3,388,144 | 6/1968 | Musolf et al. | 260/46.5 E |
| 3,873,499 | 3/1975 | Michael et al. | 260/46.5 E |

*Primary Examiner*—Melvyn I. Marquis
*Attorney, Agent, or Firm*—Gerhard K. Adam

[57] ABSTRACT

This disclosure relates to novel silicone compounds containing alkenyl thio functional groups and their method of preparation. These compounds are useful as adhesion promoters for self-adhering silicone rubbers capable of bonding to inorganic substrates especially metals. The silicone rubber-metal composites have particular applications in semiconductor devices and in ignition systems for automobiles.

20 Claims, No Drawings

ALKENYL THIOALKYL SILICONES AND METHOD OF PREPARATION

Silicon rubber polymers are discussed in considerable detail in Rubber Technology, edited by M. Morton, 2nd Edition, 1973, Chapter 15. These materials are widely used in numerous commercial applications due to their exceptional mechanical and electrical properties under extreme temperature conditions. Representative applications include airframe and space craft body sealants, automobile spark plug boots, television corona shields and medical tubing.

Commercially available heat cured silicone rubber is made from a very high viscosity fluid or gum which is composed mainly of linear polydimethylsiloxane chains and usually contains between 3,000–10,000 dimethyl siloxy units in the average chain. Most of the gums contain vinly modified polymers in which a small number of the methyl groups of the polymer are replaced by vinyl groups to provide a vulcanizate that has increased resistance to rearrangements. The silicone rubber compounds are normally vulcanized by heat curing in the presence of one more organic peroxides.

Unfortunately, conventional silicon rubbers do not bond well to inorganic substrates especially metals, because the high molecular weight of the rubber provides few active sites available for bonding. It has been proposed to use a primer on the substrate to increase adhesion, but even after the application of presently available primers, poor bonds are formed.

In accordance with one aspect of the present invention, I have discovered a novel silicone compound useful as an adhesion promoter for self-bonding silicone rubbers. These silicone compounds contain alkylenethio functional groups and are represented by the general formula:

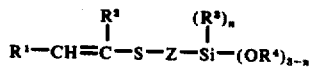     I.

wherein
R$^1$ and R$^2$ are lower alkyl, phenyl or H;
R$^3$ is alkyl, aryl or aralkyl;
R$^4$ is alkyl containing up to 15 carbon atoms, aryl or aralkyl, Z is a bivalent organic radical selected from the group consisting of alkylene having 1–18 carbon atoms, arylene, a radical having the structure

wherein
Y is oxygen or sulfur
R$^5$ is lower alkyl, or phenyl
R$^6$ is lower alkyl or phenyl and $n$ is an integer having a value of 0–2.

The addition of these compounds to conventional silicone rubbers in an effective amount of about 0.1–3.0 percent by weight produces a self-bonding rubber.

In another aspect of the invention I have discovered that the above novel silicone compounds can be polymerized to form polysiloxanes of the general formula:

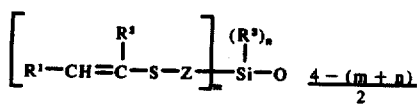     II.

wherein
R$^1$, R$^2$, R$^3$, and Z have the definitions given hereinabove, $n$ is an integer having a value of 0–2, $m$ is an integer having a value of 1 or 2, and the value of ($m+n$) is equal to 1–3.

These compounds are useful in forming copolymers with other organic polymers by vinyl polymerization and impart antiradiation properties, stability to u.v. light, and resistance to corona discharge. The improvement in using a siloxane containing a vinylthio group over a compound containing merely a vinyl group is that the former is substantially more reactive. Thus copolymers can be formed with organic vinyl monomers very readily, whereas vinyl silicones would be very reluctant to undergo the same reaction. Furthermore ionic or free radical catalyzed addition reaction across the vinylthioalkyl silicones in considerably faster than the same types of reactions involving vinyl silicones, so that further chemical transformation, if desired, is enhanced. Examples of such reactions involve the addition of alcohols, hydrogen halides, dialkylphosphites, etc.

A typical silicone rubber formulation contains the
1. silicone polymer;
2. reinforcing fillers, such as fumed silicas and carbon black;
3. extending fillers such as ground silica, calcined kaolin, calcined diatomaceous silica, calcium carbonate, zirconium carbonate, and zinc oxide;
4. additives, such as (a) inorganic coloring pigments especially iron oxide which also serves as a heat aging additive, (b) processing aids (used with highly reinforced silica fillers) which have a softening or plasticizing effect and retard creep aging.
5. blowing agents such as Unicel ND and Nitrosan
6. curing agents such as organic peroxides, e.g. benzoyl peroxide and dicumyl peroxide Such formulations and description of additives are disclosed in Morton et al reference cited above. In general all the ingredients of the typical silicone rubber formulation can be incorporated in the self bonding silicone rubber of the present invention.

One unique aspect of my invention is the incorporation into the silicone rubber formulation of about 0.1–3.0 per cent by weight of the adhesion promoter of formula I. Representative silanes are as follows:
vinylthiopropyltrimethoxysilane
vinylthiopropylmethyldiethoxysilane
vinylthiophenyldimethylethoxysilane
propenylthiopropyltrimethoxysilane
2-butenylthioethyltriethoxysilane
vinylthioethylthioethyltrimethoxysilane
vinylthiopropoxypropyltrimethoxysilane
vinylthioethylphenyldiethoxysilane
vinylthiopropyltriphenoxysilane
vinylthiopropylbenzyldimethoxysilane
styrylthiopropyltrimethoxysilane
vinylthiophenoxyphenyltrimethoxysilane
bis(vinylthiopropyl)-tetramethyldisiloxane   2,4,6,8-tetramethyl-2,4,6,8-(tetravinylthiopropyl) cyclotetrasiloxane
bis(propenylthioethyl)-tetraphenyldisiloxane
vinylthiopropylsilicone sesquioxide
silanol capped methylvinylthiopropylpolysiloxane
vinylthioethylthioethyltrimethoxysilane Usually, less than 0.1 per cent by weight of the novel adhesion promoter does not provide adequate adhesion of the silicone rubber to metal substrates, whereas more than 3.0 per cent, while generally not harmful, is considered to be undesirable from an economic standpoint.

There are a number of methods of making the novel alkenylthioalkylsilicones of my invention. A preferred method involves the vinylation with acetylene of silylmercaptans in the presence of a base catalyst as shown in the following equation:

EQUATION A

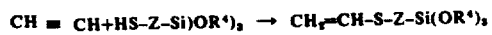

The starting materials, in the reaction of Equation A, are compounds designated as silylmercaptans as shown in formula I above. A typical compound, commercially available as a clear liquid under the designation of A-189 from the Union Carbide Corporation, is gamma-mercaptopropyltrimethoxysilane having the formula: $HS(CH_2)_3 Si(OCH_3)_3$. Other silylmercaptans which can be used as starting materials are:

mercaptopropylmethyldiethoxysilane
mercaptophenyldimethylethoxysilane
mercaptoethyltriethoxysilane
mercaptoethylthioethyltrimethoxysilane
mercaptopropyloxypropyltriethoxysilane
mercaptoethyldiethoxyphenylsilane
mercaptopropyltriphenoxysilane
mercaptopropylbenxyldimethoxysilane
p-mercaptophenoxyphenyltrimethoxysilane
1,3 bis(mercaptopropyl) tetramethyldisiloxane
2,4,6,8-tetramethyl-2,4,6,8-tetramercaptopropyl-cyclotetrasiloxane
1,3-bis(mercaptoethyl)-tetraphenyldisiloxane mercaptopropylsilicone sesquioxide The silylmercaptan in the presence or absence of a suitable solvent is reacted with acetylene in the presence of a base catalyst at elevated temperatures, e.g. 100° C, and under a suitable pressure, e.g. 700 psi. When the silylmercaptan is in the form of a liquid, no solvent is usually required. However, since the reaction must be performed in the liquid state, a suitable solvent is required when the silylmercaptan is normally in the form of a solid. Suitable organic solvents should be inert to mercaptans and acetylene, and stable to bases. Water, unsaturated and acidic solvents, and primary and secondary amines should not be used. Suitable solvents include alcohols, e.g., ethanol; hydrocarbons, e.g., toluene, hexane; ethers, e.g., tetrahydrofuran, diethyl ether; sulfones, e.g., sulfolane; chlorinated hydrocarbons, e.g., chlorobenzene, dichlorobenzene; nitriles, e.g., acetonitrile, benzonitrile; nitrohydrocarbons, e.g., nitrobenzene, nitromethane; tertiary amines, e.g., pyridine; esthers, e.g., ethyl acetate.

The vinylation reaction occurs in the presence of catalytic amount of a base catalyst. Suitable base catalysts include alkali acetylides, e.g., sodium acetylide, lithium acetylide; alkali metals, e.g., sodium, potassium; alkali alkoxide, sodium methoxide, potassium t-butoxide; alkali metal hydrides, sodium hydride, potassium hydride; alkali metal amides, sodium amide, potassium amide; alkali metal alkyls and/or aryls, i.e., phenyl sodium, methyl sodium.

Alternatively, in forming compounds wherein $R^1$ is an organic radical other than hydrogen, substituted acetylenics should be added to the silylmercaptan by a free radical mechanism. The reaction occurs according to the following method:

EQUATION B

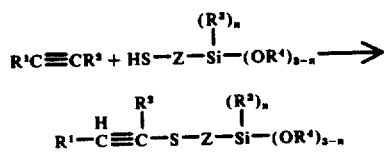

wherein the symbols $R^1$, $R^2$, $R^3$, $R^4$, Z, and n are as defined hereinabove. The conditions for the reaction are conventional and are well known in the art. In this reaction, the mercaptan and the substituted acetylene (in excess to favor mono addition) are combined in an inert solvent usually a hydrocarbon in the presence of a free radical source, such as peroxide, azo catalyst, u.v. light, etc. under an inert atmosphere and heated to about 80°–100° C for a period of 1–4 hours. The course of the reaction is conveniently monitored by gas chromatography. Upon reaction completeness, fractionation, cyrstalization, etc. techniques are employed for purifications.

Substituted acetylene compounds which can be used in the reaction include 2-butyne, propyne, phenylacetylene, 1-hexyne, 1-nonyne, 3-hexyne, 1-butyne, p-chlorophenylacetylene, 1,2 -diphenylacetylene, iodoacetylene, trimethylsilylacetylene.

Thereafter, the polymer, i.e. the alkenylthioalkylpolysiloxanes, are prepared from the monomers by a dilute acid hydrolysis according to the following reaction:

EQUATION C

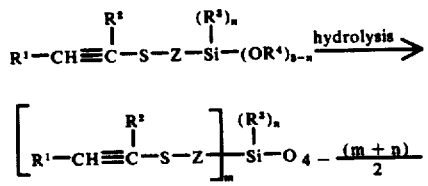

The hydrolysis is performed by placing the vinylthioakylalkoxysilane in dilute acid solution and agitating the mixture for several hours at room temperature. Thereafter, the partially condensed silanol product is extracted with an organic solvent, e.g. benzene, a trace of catalyst is added, e.g. iodine, and the condensation is completed by azeotropically removing the water with return of solvent. The course of the reaction is conveniently followed by i.r. or nuclear magnetic resonance. Upon reaction completeness, the solvent is stripped away leaving behind the vinyl thioalkylsiloxane fluids.

As an alternative procedure for preparing the polymer, a mercaptoalkyl fluid is prepared by the hydrolysis of the mercaptoalkylalkoxysilane in dilute acid solution and is subjected to vinylation with acetylene or its derivitive as in the synthesis of the monomeric materials.

My invention is further illustrated by the following examples:

EXAMPLE I

In an autoclave was placed 98 g. mercaptopropyltrimethoxysilane (0.5 mole) and then 0.4 g. potassium metal was added under a nitrogen atmosphere. When complete solution occurred and hydrogen gas no longer evolved, the autoclave was sealed. The bomb was placed in a liquid nitrogen bath and evacuated. The vacuum was broken by the admittance of nitrogen. This procedure was repeated five times to ensure complete air removal. The bomb was then placed in a rocker oven and was pressurized to 300 lb./in.$^2$ with nitrogen at room temperature.

Thereafter, acetylene was introduced until the pressure was 700 lb./in.$^2$. The bomb was then heated to 90° C, while agitation was initiated. As the pressure dropped, additional acetylene was introduced. When the pressure remained constant, the reaction was allowed to proceed for an additional 6 hours. Then the reactor was cooled, excess pressure was released and the contents of the reactor were transferred to distillation apparatus.

Upon fractionation, there was obtained 66 g. of a colorless liquid b.p. 78°/0.1 mm which was identified as vinylthiopropyltrimethoxysilane. Gas chromatography showed its purity to be > 99 per cent. An i.r. analysis confirmed its structure having bands at 6.3$\mu$, 8$\mu$, and 10.4$\mu$ which is characteristic of vinyl absorption in addition to the absorption peaks characteristic of the alkoxysilane. Its odor was not characteristic of a sulfur compound.

EXAMPLE II

A reaction flask was charged with 19.6 g. mercaptopropyltrimethoxysilane (0.1 mole) and 16.4 g. 1-hexyne (0.2 mole). It was placed under a nitrogen atmosphere while 0.5 g. benzoyl peroxide was added. The reaction mixture was heated to 90° C for a period of 4 hours while being monitored by gas chromotography.

The major product was a monoadduct. The product was then isolated by fractionation and its structure confirmed as n-hex-1-enylthiopropyltrimethoxysilane by i.r. and $C_{13}$ nmr. The yield obtained was 72 per cent.

EXAMPLE III

1-Methylpropenyl allyl sulfide was prepared by the free radical catalyzed addition of allyl mercaptan to 2-butyne.

Into a three necked flask equipped with a thermometer, addition funnel, condensor, and magnetic stirring bar and placed under a nitrogen atmosphere is placed 128 g. 1-methylpropenyl allyl sulfide and $10^{-4}$ mole of platinum as chloroplatinic acid. The reaction mixture is then heated to 120° C whereupon the dropwise addition of 134 g. trichlorosilane is initiated. Very little exotherm is noted. Upon complete addition, the reflux temperature drops to about 55° C. The reaction is allowed to proceed at reflux for 10 hours. Gas chromotography shows an adduct is formed.

The excess chlorosilane is removed followed by the addition of methyl orthoformate sufficient to convert all the chlorine silicon bonds to methoxy silicone bonds (1mole of methyl orthoformate per chlorine silicone bond).

The product, 1-methylpropenylthiopropyltrimethoxysilane, is recovered by fractionation and its structure confirmed by i.r. and $C_{13}$ nmr.

EXAMPLE IV

Mercaptoethylethioethyltrimethoxysilane was prepared by slowly adding vinyltrimethoxylsilane 74 parts (0.5 mole) to an excess of 1,2-ethylene dithiol 56.4 parts (0.6 mole) at a temperature of 95° C. An exothermic reaction occurred and the reaction temperature is maintained to 125° C by controlling the rate of silane addition.

After complete addition, gas chromotography indicated that in addition to the desired reaction product, there is also formed 1,8-bis(trimethoxysilyl)-2,6-dithishexane. The mercaptoethylthioethyltrimethoxysilane is recovered by fractionation as a colorless liquid.

Vinylation of the mercaptoethylthioethyltrimethoxysilane is then performed in accordance with the procedure described in Example I above.

EXAMPLE V

A conductive polymer system was prepared containing a polydimethylsiloxane having a molecular weight of approximately 500,000, having a conductive carbon filler incorporated therein and catalyzed with an organic peroxide. To this system was added various amounts of vinylthiopropyltrimethoxysilane according to the following formulation wherein the amounts are given in parts by weight:

| Formulation | A | B | C |
| --- | --- | --- | --- |
| Conductive silicone rubber | 100 | 100 | 100 |
| Vinylthiopropyltrimethoxysilane* | 0 | 0.5 | 1.0 |
| Organic peroxide | 1.5 | 1.5 | 1.5 |

*Samples were prepared using both the curde and the distilled form.

Bonding studies were then made on substrates panels of copper and steel. The conductive rubber was pressed in a compression mold for 15 minutes at a pressure of 2,000 lbs. and a temperature of 350° F onto the metal panels. Samples were allowed to cool for 15 minutes and then the bonds were evaluated.

The samples containing no bonding additive as shown in formulation A had 0 per cent cohesive failure, i.e. there was no bonding. Th formulations B and C containing the bonding additive showed no adhesive failure. The physical properties of the conductive silicone rubbers are moderate and the pull on the bond exceeded 50 lbs./in. the maximum level was not determined and it is highly probable that a much stronger bond could be achieved with higher levels of the vinylthiopropyltrimethoxysilane.

It was furter observed that a comparison of the adhesive properties, of samples prepared using the crude form and the distilled form of the vinylthiopropyltrimethoxysilane, indicated that the crude form gave the best results. This is probably a function of the compounding technique.

EXAMPLE VI

To 300 ml. of a 0.01 N solution of hydrochloric acid was added 30 g. of vinylthiopropylmethyldimethoxysilane. The mixture was stirred at room temperature for a period of 6 hours. Following this, the product was extracted three times each with 50 ml. benzene. To the combined extracts was added a crystal of iodine and condensation of the silanol groups was completed by refluxing the solution with continuous water removal, azeotropically, via a Dean Stark trap. When water no longer evolved (4–6 hours) the benzene was removed at atmospheric pressure, the last trace quantity being removed at a reduced pressure of 0.1 mm. The product remaining behind was a viscous fluid. Its structure was confirmed by i.r. having both siloxane and vinyltio absorption bands. There was only a faint silanol absorption band indicating silanol condensation was predominant. The silicon alkoxy bands were gone.

EXAMPLE VII

A sample of 1,3-bis(mercaptoethyl)tetramethyldisiloxane is prepared by the procedure published by Marvel and Cripps in J. Polymer Sci., 9, 53 (1952). This material is vinylated by the procedure given in example I. The product is a distillable liquid and its structure confirmed by nmr and i.r. spectroscopy.

It will be appreciated that the invention is not limited to the specific details shown in the examples and illustrations and that various modifications may be made within the ordinary skill in the art without departing from the spirit and scope of the invention.

I claim:

1. A silicone compound having alkylenethio functional groups and represented by the formula:

$$R^1CH=C(R^2)-S-Z-Si(R^3)_n(OR^4)_{3-n}$$

wherein $R^1$ and $R^2$ are lower alkyl, phenyl or hydrogen; $R^3$ is lower alkyl, phenyl or phenylalkyl; $R^4$ is alkyl containing up to 15 carbon atoms, phenyl or phenylalkyl; Z is a bivalent organic radical selected from the group consisting of alkylene having 1-18 carbon atoms, phenylene, a radical having the structure: $-R^5-Y-R^6-$ wherein Y is oxygen or sulfur, $R^5$ is lower alkylene or phenylene, $R^6$ is lower alkylene or phenylene and n is an integer having the value of 0-2.

2. The product of claim 1, wherein $R^1$, $R^2$, $R^3$ and $R^4$ are lower alkyl, Z is a radical having the structure $-R^5-Y-R^6$ wherein $R^5$ and $R^6$ are lower alkylene and Y if sulfur.

3. The product of claim 1, wherein said compound is vinylthiopropyltrimethoxysilane.

4. The product of claim 1, wherein said compound is vinylthiopropylmethyldiethoxysilane.

5. The product of claim 1, wherein said compound is vinylthiophenyldimethylethoxysilane.

6. The product of claim 1, wherein said compound is propenylthiopropyltrimethoxysilane.

7. The product of claim 2, wherein said compound is vinylthioethylthioethyltrimethoxysilane.

8. A self bonding silicone rubber comprising a silicone polymer characterized by being composed mainly of linear polydimethysiloxane chains and having between 3,000–10,000 dimethyl siloxy units in the average chain, and 0.1 – 3.0 percent by weight of a silicone compound having alkylenethio functional groups and represented by the formula:

$$R^1CH=C(R^2)-S-Z-Si(R^3)_n(OR^4)_{3-n}$$

wherein $R^1$ and $R^2$ are lower alkyl, phenyl or hydrogen; $R^3$ is lower alkyl, phenyl or phenylakyl; $R^4$ is alkyl containing up to 15 carbon atoms, phenyl, or phenylalkyl; Z is a bivalent organic radical selected from the group consisting of alkylene having 1-18 carbon atoms, phenylene, a radical having the structure: $-R^5-Y-R^6-$ wherein Y is oxygen or sulfur, $R^5$ is lower alkylene or phenylene, $R^6$ is lower alkylene or phenylene and n is an integer having a value of 0-2.

9. The silicone rubber of claim 8, wherein said compound is vinylthiopropyltrimethoxysilane.

10. The silicone rubber of claim 8, wherein said compound is vinylthiopropylmethyldiethoxysilane.

11. the silicone rubber of claim 8, wherein said compound is vinylthiophenyldimethylethoxysilane.

12. The silicone rubber of claim 8, wherein said compound is propenylthiopropyltrimethoxysilane.

13. The silicone rubber of claim 8, wherein said compound is vinylthioethylthioethyltrimethoxysilane.

14. A polysiloxane having the general formula:

$$\left[R^1-CH=C(R^2)-S-Z\right]_m Si(R^3)_n O_{\frac{4-(m+n)}{2}}$$

wherein $R^1$ and $R^2$ are lower alkyl, phenyl, or hydrogen; $R^3$ is lower alkyl, phenyl, or phenylalkyl; Z is a bivalent organic radial selected from the group consisting of alkylene having 1-18 carbon atoms, phenylene, a radical having the structure: $-R^5-Y-R^6-$, wherein Y is oxygen or sulfur, $R^5$ is lower alkylene or phenylene, $R^6$ is lower alkylene or phenylene; n is an integer having a value of 0-2, m is an integer having a value of 1 or 2, and the value of (m+n) is equal to 1-3.

15. The polysiloxane of claim 14, wherein m has a value of 1 and n has a value of 2.

16. The product of claim 15, wherein said polysiloxane is 1,3-bis(vinylthiopropyltetramethyldisiloxane.

17. The product of claim 15, wherein said polysiloxane is 1,3-bis(vinylthioethyltetramethyldisiloxane.

18. The polysiloxane of claim 14, wherein m and n each have a value of 1.

19. The product of claim 18, wherein said poylsiloxane is 2,4,6,8-tetrakis(vinylthiopropyl)-2,4,6,8-tetramethylcyclotetrasiloxane.

20. The product of claim 18, wherein said polysiloxane is 2,4,6,8-tetrakis(vinylthioethyl)-2,4,6,8-tetramethylcyclotetrasiloxane.

* * * * *